(12) United States Patent
Abhari

(10) Patent No.: US 8,058,484 B2
(45) Date of Patent: Nov. 15, 2011

(54) FLEXIBLE GLYCEROL CONVERSION PROCESS

(75) Inventor: Ramin Abhari, Bixby, OK (US)

(73) Assignee: Syntroleum Corporation, Tulsa, OK (US)

( * ) Notice: Subject to any disclaimer, the term of this patent is extended or adjusted under 35 U.S.C. 154(b) by 601 days.

(21) Appl. No.: 12/196,426

(22) Filed: Aug. 22, 2008

(65) Prior Publication Data
US 2009/0054701 A1 Feb. 26, 2009

Related U.S. Application Data

(60) Provisional application No. 60/957,935, filed on Aug. 24, 2007.

(51) Int. Cl.
 *C07C 27/04* (2006.01)
(52) U.S. Cl. ....................................... 568/861
(58) Field of Classification Search .................. 568/861
See application file for complete search history.

(56) References Cited

U.S. PATENT DOCUMENTS

| | | | |
|---|---|---|---|
| 2,163,563 A | 6/1939 | Schrauth | |
| 4,642,394 A | 2/1987 | Che | |
| 4,992,605 A | 2/1991 | Craig et al. | |
| 5,214,219 A | 5/1993 | Casale et al. | |
| 5,616,817 A | 4/1997 | Schuster et al. | |
| 5,705,722 A | 1/1998 | Monnier et al. | |
| 5,851,338 A | 12/1998 | Pushaw | |
| 6,855,410 B2 | 2/2005 | Buckley | |
| 7,232,935 B2 | 6/2007 | Myllyoja et al. | |
| 2004/0055209 A1 | 3/2004 | Jakkula et al. | |
| 2004/0230085 A1 | 11/2004 | Jakkula et al. | |
| 2005/0244312 A1 | 11/2005 | Suppes et al. | |
| 2006/0161032 A1 | 7/2006 | Murzin et al. | |
| 2006/0186020 A1 | 8/2006 | Gomes | |
| 2006/0199984 A1 | 9/2006 | Kuechler et al. | |
| 2006/0207166 A1 | 9/2006 | Herskowitz et al. | |
| 2006/0264684 A1 | 11/2006 | Petri et al. | |
| 2007/0006523 A1 | 1/2007 | Myllyoja et al. | |
| 2007/0010682 A1 | 1/2007 | Myllyoja et al. | |
| 2007/0170091 A1 | 7/2007 | Monnier et al. | |

FOREIGN PATENT DOCUMENTS

| | | |
|---|---|---|
| EP | 1728844 | 12/2006 |
| SE | 9700149 | 8/1997 |
| WO | WO 00/11117 | 3/2000 |
| WO | WO 2004/104142 | 12/2004 |
| WO | WO 2005/026297 | 3/2005 |
| WO | WO 2007/068795 | 6/2007 |

OTHER PUBLICATIONS

Wang, Keyi; Hawley, Martin C.; DeAthos, Scott J.; Ind. Eng. Chem. Res. 2003, 42, 2913-2923.

Sharma, S.D.; Sagara, K. "Latent Heat Storage Materials and Systems: A Review", International Journal of Green Energy, 2: 1-56, 2005.

Wong, A. Monnier, J.; Stumborg, M.; Hogan E. Technical and Economic Aspects of Manufacturing Cetane-Enhanced Diesel Fuel from Canola Oil ; Bio-oils Symposium: Saskatoon, Saskatchewan, Canada; Mar. 2-3, 1994.

*Primary Examiner* — Sikarl Witherspoon
(74) *Attorney, Agent, or Firm* — Hall Estill Law Firm

(57) ABSTRACT

The present invention relates to a process for converting byproducts of the manufacture of biodiesel into industrially useful oxygenated products of greater commercial value. The process includes a trickle bed reactor in which a glycerol-rich feedstock is reacted with hydrogen in the presence of a nickel-tungsten catalyst under typical refining condition of high temperature and pressure, yielding propane synfuel or propanediols.

10 Claims, 1 Drawing Sheet

FLEXIBLE GLYCEROL CONVERSION PROCESS

CROSS REFERENCE TO RELATED APPLICATIONS

The present patent application claims priority to the provisional patent application identified by U.S. Pat. No. 60/957,935 filed Aug. 24, 2007, the entire content of which is hereby incorporated herein by reference.

FIELD OF INVENTION

The present invention relates to a process for converting the byproducts of the manufacture of biodiesel into industrially useful oxygenated products of greater commercial value. In particular, this process may be used to convert glycerol into propane synfuel, or propylene glycol and 1,3-propanediol, depending on the temperature at which the process is conducted. The invention further relates to the use of a macropore nickel tungsten catalyst.

BACKGROUND OF INVENTION

Glycerol (more commonly known as glycerin) is a byproduct of the biodiesel manufacturing process. As the biodiesel industry has expanded, glycerol has suffered a dramatic price decrease. Industry analysts believe that the future economic viability of the biodiesel industry depends on creation of new markets and applications for glycerol.

A number of processes have been developed to convert glycerol into propylene glycol, a commodity petrochemical. Conventional processing of natural glycerol into propanediols such as propylene glycol uses a catalyst reacted with the glycerol and hydrogen under temperature conditions up to 540° F. and pressure conditions up to 15,000 psi. The catalysts generally include metals or mixtures of metals including: ruthenium, nickel, zinc/copper, cobalt/copper/manganese/molybdenum, cobalt/copper/manganese, copper chromite, barium oxide, manganese oxide, platinum, palladium, and tungsten in combination with a Group VII metal (iron, cobalt, nickel, ruthenium, rhodium, palladium, osmium, or platinum). Many of these processes produce byproducts that are of low value or of very limited demand. Other processes produce high value byproducts in addition to propylene glycol, but involve complex mixtures of solvents and pH modifiers that may make these processes less robust and consequently impractical to implement on a large scale. In addition, all of the above processes are optimized to produce a single product or set of products, and cannot be modified to convert glycerol into value-added products other than propanediols. Clearly, there is an unmet need for a simple and flexible process to convert glycerol to high value/high demand products.

SUMMARY OF THE INVENTION

The present invention relates to a process to convert glycerol into products of greater commercial value. The process includes reacting glycerol and hydrogen in the presence of a catalyst, containing a mixture of tungsten and nickel, under conditions of high temperature and pressure. The products resulting from this process include propylene glycol, 1,3 propanediol, and propane synfuel. The process may be implemented in a trickle-bed reactor, and the operating temperature of the process may be manipulated to control the products resulting from the hydrogenation of glycerol in this process. At higher reactor temperatures, the process may operate in a "synfuel mode", converting glycerol to propane synfuel, or at lower reactor temperatures, the process may operate in a "chemicals mode", producing propylene glycol and high value 1,3-propanediol as co-products. These glycerol conversion paths are shown in FIG. 1.

The glycerol-containing feedstocks may include those that are produced from bio-renewable resources, such as vegetable oils. The feedstock may, for example, be provided as the crude glycerol byproduct of the manufacture of biodiesel, or the glycerol may be separated from these crude glycerol byproducts using known processes, such as simple-path distillation or treatment with ion exchangers.

DETAILED DESCRIPTION OF THE INVENTION

Figure 1:
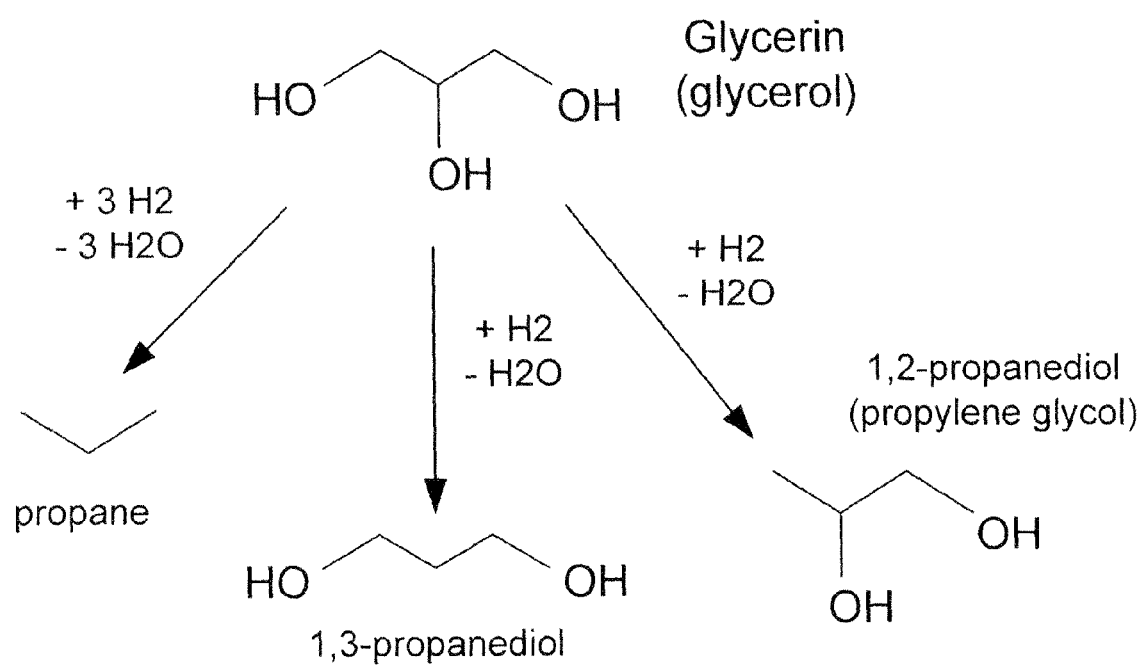
FIG. 1 is a schematic showing the chemical paths of a process of the present invention.

The present invention relates to a process for converting glycerol-containing feedstock into propane synfuel and propanediols. The process is initiated by hydrogenating the glycerol-containing feedstock by reacting the glycerol with hydrogen in the presence of a nickel/tungsten catalyst under typical refining pressure and temperature conditions. The product resulting from the process of the present invention is predominantly propane synfuel at temperatures above about 600° F., and are predominantly propanediols at temperatures below about 600° F.

The glycerol feedstock may be obtained from the transesterification of fats and oils used in the manufacture of biodiesel. The biodiesel byproducts may be used as feedstock without further processing or contaminants may be separated from the biodiesel byproducts using processes known by one of ordinary skill in the art including simple path distillation or treatment with ion exchangers.

The products resulting from the process of the present invention are propane synfuel, and propanediols consisting of propylene glycol (1,2-propanediol) and high value 1,3-propanediol. Simple path distillation may be used to separate the desired products from other byproducts such as unreacted glycerol, n-propanol, acetol, and other lower alcohols. Propane is useful as fuel, propylene glycol has many uses as an anti-freezing additive, a de-icer and as a moisturizer in many cosmetic and other personal care products. 1,3-propanediol may be formulated into a variety of industrial products including composites, adhesives, laminates, coatings, moldings, novel aliphatic polyesters, copolyesters, solvents, anti-freeze and other uses.

The catalyst in the process is a hydrogenation catalyst suitable for hydrogenating a glycerol into either propane or a mixture of 1,2-propanediol (propylene glycol) and 1,3-propanediol. The catalysts are based on the elements tungsten and nickel and will include a carrier. The catalytic element may include between about 1% and about 99% of the total catalyst weight, preferably between about 50% and about 85% of the total catalyst weight. The catalytic elements may also be supported on a non-reactive, inorganic support such as alumina, magnesium oxide, silica and combinations thereof. The element can be supported on an inorganic support by any means known to one of ordinary skill in the art such as, for example, impregnation, coprecipitation, ion exchange, and combinations of two or more thereof. If the catalytic element is supported on an inorganic support or is a component of an alloy or a solid solution, the catalytic element is generally present in a range of between about 0.1% and about 60% of the total catalyst weight and preferably between about 1% and about 50% of the total catalyst weight.

The catalyst can be present in any appropriate physical shape or form. It can be in fluidizable forms, extrudates, tablets, spheres, or combinations of two or more thereof. When employing the process of the present invention using a fixed bed catalyst, the catalyst is in the form of granules having a particle size in the range of between about 0.76 mm and about 10.2 mm (about 0.03 to about 0.40 inch). When employing the process of the present invention using a slurry-phase catalyst, the catalyst is in finely divided form, preferably less than about 100 μm in size, the most preferred range being between about 20 μm and about 75 μm.

The catalysts may be in the oxide form and sulfided during startup, or presulfided and active when loaded into a reactor. The catalyst may be modified with sulfides beforehand during its preparation, or in situ by the addition of a compound that acts as source of sulfur. For this purpose, preferred sulfurated compounds are sodium sulfide, bisulfates, for example, sodium bisulfates and thiosulfates. The ratio of sulfur ions to tungsten/nickel is generally between about 0.2 and about 5.0 moles of sulfur ions per mole of tungsten/nickel. The surface texture of the catalyst in the most preferred embodiment is a high macropore texture, herein defined as a pore diameter distribution whereby approximately 50% of the total pore volume of the catalyst is present as macropores of diameter greater than about 100 Å.

In one embodiment, the process reactor is run at a typical refining temperature, between about 300° F. and about 850° F. For running in the "synfuel mode", in which the products of the process are predominantly propane synfuel, the preferred operating temperature of the reactor is approximately 650° F. For running in the "chemical mode", in which the products of the process of predominantly propanediols, the preferred operating temperature of the reactor is approximately 550° F. The process reactor of the present invention may also run at a typical refining pressure, between about 250 psig to about 3,000 psig. Although the efficiency of the process of the present invention may be relatively insensitive to changes in the operating pressure, the preferred operating pressure is between about 1,500 psig and about 2,300 psig.

In one embodiment, the process to convert glycerol is run using a trickle bed reactor, defined herein as a tubular reactor in which the catalyst is fixed while the reactants are added at the top of the reactor and flow to the bottom where the product is continuously withdrawn. The glycerol feedstock is added to the reactor at a rate of about 0.5 to about 0.9 LHSV, with the most preferred rate of addition of glycerol feedstock being about 0.65 LHSV. Optionally, hydrogen is added to the reactor at a rate of between about 10,000 and about 30,000 scf/bbl, with a most preferred rate of 20,000 scf/bbl.

In order to further illustrate the present invention, the following examples are given. However, it is to be understood that the examples are for illustrative purposes only and are not to be construed as limiting the scope of the subject invention.

EXAMPLES

Example 1

Complete Conversion of Glycerol to Propane Synfuel was Successfully Demonstrated in a Pilot Study To assess the feasibility of converting glycerol into propane using a process of catalytic conversion, a pilot study was conducted using a pilot scale tubular reactor. The reactor was loaded with 80 cubic centimeters of high macro-pore (34% of pores>100 Å) nickel-tungsten catalyst. The catalyst was sulfided to further modify the catalyst, and the reactor was started up in trickle-bed mode using a feedstock of 98% pure glycerol (Sigma-Aldrich, St. Louis, Mo.). Glycerol was supplied to the reactor at a flow rate of 0.65 LHSV, and hydrogen was supplied to the reactor at a pressure of 2,200 psig and at a flow rate of 20,000 scf/bbl. The operating temperature of the reactor during this experiment was set at 650° F. Gas phase products were collected and analyzed using an online gas chromatography instrument, and the resulting liquid phase products were also collected and analyzed using gas chromatography-mass spectrometry.

The masses of reactants and products were closely monitored, and a mass balance closure of 100.4% was achieved for the experiment. The propane synfuel yielded by the reactor under these conditions amounted to 26.6% of the total mass of the glycerol feedstock, corresponding to 55% of the maximum theoretical yield. Water produced by the reaction accounted for 44.8% of the total mass of the glycerol feedstock. The total liquid product (TLP), recovered after flashing off the water, accounted for 8.7% of the reactant mass. Analysis of the TLP using gas chromatography-mass spectrometry determined that no residual glycerol remained in the liquid product, indicating that the glycerol fed into the reactor was completely converted into reaction products. The results of this pilot study demonstrate that glycerol can be specifically converted to propane synfuel in an efficient manner.

Example 2

The Conversion of Glycerol to Propane Synfuel was Sensitive to the Metals Contained in the Catalyst Used in the Reactor To assess the effect of the composition of the catalyst on the process of converting glycerol into propane, a study was conducted using a pilot scale tubular reactor. The reactor was loaded with 80 cubic centimeters of nickel molybdenum catalyst. The catalyst was sulfided to further modify the catalyst, and the reactor was started up in the trickle-bed mode using a feedstock of 98% pure glycerol (Sigma-Aldrich, St. Louis, Mo.). Glycerol was supplied to the reactor at a flow rate of 0.65 LHSV, and hydrogen was supplied to the reactor at a pressure of 2,200 psig and at a flow rate of 20,000 scf/bbl. The operating temperature of the reactor during this experiment was set at 650° F. The gas phase product was analyzed using an online gas chromatography instrument, and the resulting liquid phase products were also collected and analyzed using gas chromatography-mass spectrometry.

The propane synfuel yielded by the reactor under these conditions amounted to 1-2% of the total mass of the glycerol feedstock, or approximately 2-4% of the maximum theoretical yield. The mass of the reactants and products was closely monitored, and a very low mass balance closure was achieved for the study, suggesting that the majority of the gas components produced by the study were species that were not detectible by a standard refinery gas analyzer such as CO, $CO_2$, and C1-C6+ hydrocarbons. The results of this experiment demonstrate that the process of converting glycerol to propane synfuel is sensitive to the metal composition of the catalyst.

Example 3

The Catalytic Conversion of Glycerol to Propane Synfuel is not Sensitive to the Surface Texture of the Catalyst To assess the sensitivity of converting glycerol into propane synfuel using catalytic hydrogenation to the density of pores on the surface of the catalyst, a study was conducted using a pilot scale tubular reactor. The reactor was loaded with 80 cubic centimeters of low pore nickel-tungsten catalyst. The catalyst was sulfided to further modify the catalyst, and the reactor was started up in the trickle-bed mode using a feedstock of 98% pure glycerol (Sigma-Aldrich, St. Louis, Mo.). Glycerol was supplied to the reactor at a flow rate of 0.65 LHSV, and hydrogen was supplied to the reactor at a pressure of 2,200 psig and at a flow rate of 20,000 scf/bbl. The operating temperature of the reactor during this experiment was set at 650° F. Gas phase products were collected and analyzed using an online gas chromatography instrument, and the resulting liquid phase products were also collected and analyzed using gas chromatography-mass spectrometry.

The propane synfuel yielded by the tubular reactor under these conditions amounted to 27.9% of the total mass of the glycerol feedstock, corresponding to 58% of the maximum theoretical yield, which was very similar to the amount of propane synfuel produced using the high macro-pore nickel-tungsten catalyst under otherwise identical conditions (see Example 1). The results of this study demonstrate that the surface texture of the catalyst, as expressed by the density of macropores and micropores of the catalyst, has little effect on the effectiveness of catalyst in converting glycerol to propane synfuel.

Example 4

The Products Resulting from the Catalytic Hydrogenation of Glycerol are a Function of the Operating Temperature of the Reactor To assess the effect of reactor operating temperature on the process of catalytic hydrogenation of glycerol, a study was conducted using a pilot scale tubular reactor. The reactor was loaded with 80 cubic centimeters of high macro-pore nickel-tungsten catalyst. The catalyst was sulfided to further modify the catalyst, and the reactor was started up in the trickle-bed mode using a feedstock of 98% pure glycerol (Sigma-Aldrich, St. Louis, Mo.). Glycerol was supplied to the reactor at a flow rate of 0.65 LHSV, and hydrogen was supplied to the reactor at a pressure of 2,200 psig and at a flow rate of 20,000 scf/bbl. The operating temperature of the reactor during this experiment was set at 550° F. Gas phase products were collected and analyzed using an online gas chromatography instrument, and the resulting liquid phase products were also collected and analyzed using gas chromatography-mass spectrometry.

The propane synfuel yielded by the reactor under these conditions amounted to 2.8% of the total mass of the gaseous products, corresponding to 5.8% of the maximum theoretical yield. The TLP, recovered after flashing off the water, accounted for 74.5% of the mass of the glycerol feedstock. Analysis of the TLP using gas chromatography-mass spectrometry determined that 74.0% of the TLP mass was propylene glycol, and 5% of the TLP mass was 1,3-propanediol. Comparing the results of this study to the results presented in Example 1, lowering the operating temperature of the reactor from 650° F. to 550° F. resulted in a dramatic shift in the reaction products from predominantly gaseous propane synfuel to propylene glycol and 1,3-propanediol. The operating temperature of the reactor is a simple means of specifically controlling the products resulting from the catalytic hydrogenation of glycerol.

Example 5

The Products Resulting from the Catalytic Hydrogenation of Glycerol are not Sensitive to the Pressure Inside the Reactor To assess the effect of reactor operating pressure on the process of catalytic hydrogenation of glycerol, a study was conducted using a pilot scale tubular reactor. The reactor was loaded with 80 cubic centimeters of high macro-pore nickel-tungsten catalyst. The catalyst was sulfided to further modify the catalyst, and the reactor was started up in the trickle-bed mode using a feedstock of 98% pure glycerol (Sigma-Aldrich, St. Louis, Mo.). Glycerol was supplied to the reactor at a flow rate of 0.65 LHSV, and hydrogen was supplied to the reactor at a pressure of 1,600 psig and at a flow rate of 20,000 scf/bbl. The operating temperature of the reactor during this experiment was set at 550° F. Gas phase products were collected and analyzed using an online gas chromatography instrument, and the resulting liquid phase products were also collected and analyzed using gas chromatography-mass spectrometry.

The propane synfuel yielded by the reactor under these conditions amounted to 2.1% of the total mass of the glycerol feedstock, corresponding to 4.4% of the maximum theoretical yield. The TLP, recovered after flashing off the water, accounted for 72.5% of the mass of the glycerol feedstock. Analysis of the TLP using gas chromatography-mass spectrometry determined that the TLP mass was comprised of 67.5% propylene glycol, and 6.6% 1,3-propanediol on a mass basis. Comparing the results of this study to the results presented in Example 4, lowering the operating pressure of the reactor from 2,200 psig to 1,600 psig did not significantly affect the reaction products of the process.

Example 6

The Catalytic Conversion of Glycerol to Propylene Glycol and 1,3-propanediol is Sensitive to the Surface Texture of the Catalyst To assess the sensitivity of the process of catalytically converting glycerol into propylene glycol and 1,3-propanediol to the presence of pores on the surface of the catalyst, a study was conducted using a pilot scale tubular reactor. The reactor was loaded with 80 cubic centimeters of low macro-pore nickel-tungsten catalyst. The catalyst was sulfided to further modify the catalyst, and the reactor was started up in the trickle-bed mode using a feedstock of 98% pure glycerol (Sigma-Aldrich, St. Louis, Mo.). Glycerol was supplied to the reactor at a flow rate of 0.65 LHSV, and hydrogen was supplied to the reactor at a pressure of 2,200 psig and at a flow rate of 20,000 scf/bbl. The operating temperature of the reactor during this experiment was set at 550° F. Gas phase products were collected and analyzed using an online gas chromatography instrument, and the resulting liquid phase products were also collected and analyzed using gas chromatography-mass spectrometry.

The TLP, recovered after flashing off the water, was a two-phase liquid. Gas chromatography-mass spectrometry determined that the TLP was comprised of 65.6% propylene glycol, 22.8% unconverted glycerol, and 0% 1,3-propanediol on a mass basis. The results of this study, when compared to the results presented in Example 5, demonstrate that at conditions appropriate for the conversion of glycerol to propylene glycol and 1,3-propanediol, the reaction is relatively sensitive to the surface texture of the catalyst, as expressed by the density of macropores and micropores of the catalyst.

From the above description, it is clear that the present invention is well adapted to carry out the objects and to attain the advantages mentioned herein as well as those inherent in the invention While the invention has been explained in relation to exemplary embodiments, it is to be understood that various modifications may be made which will readily suggest themselves to those skilled in the art and which are accomplished within the spirit of the invention disclosed and claimed.

What is claimed is:

1. A process for converting glycerol for producing a product, comprising the steps of:
    providing a glycerol containing feedstock;
    reacting the glycerol containing feedstock with hydrogen in the presence of a heterogeneous catalyst wherein the catalyst used is nickel tungsten; and
    recovering the converted glycerol into a product selected from the group comprising propane, 1,3-propanediol and combinations thereof.

2. The process of claim 1 wherein a nickel tungsten catalyst surface texture is a high macropore texture.

3. The process of claim 2 wherein glycerol is contacted with the nickel tungsten catalyst in a fixed bed reactor.

4. The process of claim 3 wherein the fixed bed reactor operates in a chemical mode and a synfuel mode.

5. The process of claim 4 wherein in the synfuel mode glycerol is converted to propane synfuel.

6. The process of claim 5 wherein in the chemical mode glycerol is converted to propylene glycol and 1,3-propanediol.

7. A process for converting glycerol for producing a product, comprising the steps of: providing a glycerol containing feedstock; reacting the glycerol containing feedstock with hydrogen in the presence of a heterogeneous catalyst, wherein the catalyst used is nickel molybdenum; and recovering the converted glycerol into a product selected from the group comprising propane, 1,3-propanediol, and combinations thereof.

8. The process of claim 1 wherein glycerol is converted into propane synfuel.

9. The process of claim 1 further comprising the step of:
    heating the reaction of the glycerol containing feedstock with hydrogen in the presence of the catalyst to a temperature greater than about 600° F.

10. The process of claim 9 wherein the product resulting from the process is propane synfuel.

* * * * *